United States Patent
Podolski et al.

(10) Patent No.: US 9,161,940 B2
(45) Date of Patent: Oct. 20, 2015

(54) SELECTIVE ESTROGEN RECEPTOR MODULATORS WITH SHORT HALF-LIVES AND USES THEREOF

(71) Applicants: Joseph S. Podolski, The Woodlands, TX (US); Ronald D. Wiehle, Houston, TX (US)

(72) Inventors: Joseph S. Podolski, The Woodlands, TX (US); Ronald D. Wiehle, Houston, TX (US)

(73) Assignee: REPROS THERAPEUTICS INC., The Woodlands, TX (US)

( * ) Notice: Subject to any disclaimer, the term of this patent is extended or adjusted under 35 U.S.C. 154(b) by 0 days.

(21) Appl. No.: 14/378,573

(22) PCT Filed: Feb. 14, 2013

(86) PCT No.: PCT/US2013/026178
§ 371 (c)(1),
(2) Date: Aug. 13, 2014

(87) PCT Pub. No.: WO2013/123218
PCT Pub. Date: Aug. 22, 2013

(65) Prior Publication Data
US 2015/0031680 A1    Jan. 29, 2015

Related U.S. Application Data

(60) Provisional application No. 61/598,723, filed on Feb. 14, 2012.

(51) Int. Cl.
*A61K 31/445* (2006.01)
*A61K 31/55* (2006.01)
*A61K 31/00* (2006.01)
*A61K 31/138* (2006.01)
*A61K 31/4025* (2006.01)
*A61K 31/4535* (2006.01)

(52) U.S. Cl.
CPC ............... *A61K 31/55* (2013.01); *A61K 31/00* (2013.01); *A61K 31/138* (2013.01); *A61K 31/4025* (2013.01); *A61K 31/4535* (2013.01)

(58) Field of Classification Search
USPC .................................................. 514/317, 414
IPC ........................................................ A61K 31/445
See application file for complete search history.

(56) References Cited

U.S. PATENT DOCUMENTS 7,799,782 B2 *   9/2010   Munson et al. ............. 514/234.5
2003/0040510 A1 *  2/2003   Labrie ........................... 514/177

FOREIGN PATENT DOCUMENTS

WO         2010/054248 A1      5/2014

OTHER PUBLICATIONS

Bryant's CAS: 150: 205598, 2008.*
International Search Report of PCT/US2013/026178 dated Jul. 22, 2013.
Written Opinion of PCT/US2013/026178 dated Jul. 22, 2013.

* cited by examiner

*Primary Examiner* — Rei-Tsang Shiao
(74) *Attorney, Agent, or Firm* — Morgan, Lewis & Bockius LLP

(57) ABSTRACT

The present invention relates to the long-term administration of a selective estrogen receptor modulator (SERM) with a short half-life for the treatment of a variety of estrogen receptor-mediated conditions. The SERM may be administered at a concentration at or below that of a SERM with a long half-life in order to achieve an equivalent therapeutic effect.

12 Claims, 1 Drawing Sheet

| Subject | Enclomiphene Dose | Day 1 AUC$_{(0-24)}$ | Day 14 AUC$_{(0-24)}$ | Accumulation Index Day 14 / Day 1 AUC Ratio |
|---|---|---|---|---|
| 1008 | Enclomiphene 12.5 mg | 12.2504 | 24.7157 | 2.0175 |
| 1043 | Enclomiphene 12.5 mg | 34.4866 | 69.7163 | 2.0215 |
| 1068 | Enclomiphene 12.5 mg | 10.0064 | 37.1102 | 3.7086 |
| 1071 | Enclomiphene 12.5 mg | 10.2108 | 36.9013 | 3.6139 |
| 1096 | Enclomiphene 12.5 mg | 1.4717 | 1.8622 | 1.2653 |
| | | | Mean | 2.5254 |
| | | | SD | 1.0822 |
| | | | SE | 0.4840 |
| | | | Range | 1.27 - 3.71 |
| Subject | Enclomiphene Dose | Day 1 AUC$_{(0-24)}$ | Day 14 AUC$_{(0-24)}$ | Accumulation Index Day 14/Day 1 AUC Ratio |
| 1010 | Enclomiphene 25 mg | 33.4381 | 67.8184 | 2.0282 |
| 1039 | Enclomiphene 25 mg | 9.4452 | 29.5313 | 3.1266 |
| 1078 | Enclomiphene 25 mg | 26.2345 | 125.6074 | 4.7879 |
| 1084 | Enclomiphene 25 mg | 40.4145 | 78.4035 | 1.9400 |
| 1090 | Enclomiphene 25 mg | 100.0801 | 231.2393 | 2.3105 |
| | | | Mean | 2.8386 |
| | | | SD | 1.1859 |
| | | | SE | 0.5304 |
| | | | Range | 1.94 - 4.79 |
| Subject | Enclomiphene Dose | Day 1 AUC$_{(0-24)}$ | Day 14 AUC$_{(0-24)}$ | Accumulation Index Day 14/Day 1 AUC Ratio |
| 1001 | Enclomiphene 50 mg | 37.2391 | 108.5459 | 2.9148 |
| 1037 | Enclomiphene 50 mg | 23.2863 | 36.3181 | 1.5596 |
| 1091 | Enclomiphene 50 mg | 48.851 | 131.3707 | 2.6892 |
| 1094 | Enclomiphene 50 mg | 43.6337 | 122.8372 | 2.8152 |
| | | | Mean | 2.4947 |
| | | | SD | 0.6302 |
| | | | SE | 0.3151 |
| | | | Range | 1.56 - 2.92 |

SELECTIVE ESTROGEN RECEPTOR MODULATORS WITH SHORT HALF-LIVES AND USES THEREOF

CROSS-REFERENCE TO RELATED APPLICATIONS

This application claims the benefit of U.S. Provisional Application No. 61/598,723, filed Feb. 14, 2012, the contents of which are incorporated herein by reference.

FIELD OF THE INVENTION

The present invention relates to the long-term (i.e. chronic) administration of a selective estrogen receptor modulator with a short half-life for the treatment of a variety of estrogen receptor-mediated conditions.

BACKGROUND

Selective estrogen receptor modulators (SERMs) are a class of compounds that bind to estrogen receptors (ERs) thereby inducing specific conformational changes in the receptors. SERMS can exert different effects in different tissues resulting from tissue-specific recruitment of coactivators (which enhance ER transcriptional activity) and corepressors (which repress ER transcriptional activity). SERMs are therefore distinguished from the so called "pure" estrogen receptor agonists/antagonists that uniformly activate or block estrogen effects independent of tissue type.

SERMS, by virtue of their effect on the estrogen receptor, are useful for treating a variety of disorders having an estrogen component. Many of these disorders are chronic disorders requiring long-term administration of the SERM. However, when administered over long periods of time, serious adverse effects have been observed, limiting the usefulness of these compounds. A significant advance in the art would occur if these SERMs could be administered to treat chronic estrogen receptor-mediated disorders.

SUMMARY OF THE INVENTION

The present invention provides methods for chronic administration of SERMs which reduce or eliminate the adverse effects resulting from long-term administration. According to the methods, a pharmaceutical composition comprising an effective amount of a SERM with a short half-life or a pharmaceutically acceptable salt thereof, is administered to a patient with one or more estrogen receptor-mediated disorders in order to treat the disorder for a period of at least six months.

Examples of disorders that may be treated by chronic administration of an effective amount of a SERM with a short half-life (and which therefore may be treated according to the present invention) include, without limitation, secondary hypogonadism, type 2 diabetes, elevated cholesterol, elevated triglycerides, wasting, lipodystrophy, osteoporosis, female and male infertility, benign prostate hypertrophy, menopause, prostate cancer, breast cancer, uterine cancer and ovarian cancer.

BRIEF DESCRIPTION OF THE DRAWING

FIG. 1 Individual $AUC_{(0-24)}$ Values by Enclomiphene Dose on Days 1 and 14, Individual $AUC_{(0-24)}$ Ratios and Summary Statistics for $AUC_{(0-24)}$ Ratio. This figure depicts single dose and steady state pharmacokinetic data gathered during oral administration of trans-clomiphene at 12.5 mg, 25 mg, or 50 mg per day.

DETAILED DESCRIPTION

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any way. Embodiments illustrated under any heading may be combined with embodiments illustrated under any other heading.

It is to be understood that any ranges, ratios and ranges of ratios that can be formed by any of the numbers or data present herein represent further embodiments of the present invention. This includes ranges that can be formed that do or do not include a finite upper and/or lower boundary. Accordingly, the skilled person will appreciate that many such ratios, ranges and ranges of ratios can be unambiguously derived from the data and numbers presented herein and all represent embodiments of the invention.

Before the present compounds, compositions and methods are disclosed and described, it is to be understood that the terminology used herein is for the purpose of describing particular embodiments only and is not intended to be limiting. It must be noted that, as used in the present specification and the appended claims, the singular forms "a," "an" and "the" include plural referents unless the context clearly dictates otherwise.

Definitions

The term "oral" administration means that the active agent is in a formulation designed to be ingested, i.e. designed to be delivered to the gastrointestinal system for absorption.

The term "effective dosage" means an amount of the composition's active component sufficient to treat a particular condition.

The term "treat" or "treatment" as used herein refers to any treatment of any estrogen receptor-mediated disorder or disease, and includes, but is not limited to, inhibiting the disorder or disease arresting the development of the disorder or disease; relieving the disorder or disease, for example, causing regression of the disorder or disease; or relieving the condition caused by the disease or disorder, relieving the symptoms of the disease or disorder.

The term "prevent" or "prevention," in relation to an estrogen receptor-mediated disorder or disease, means preventing the onset of disorder or disease development if none had occurred, or preventing further disorder or disease development if the disorder or disease was already present.

The term "pharmaceutically acceptable salt" refers to a salt prepared from a pharmaceutically acceptable non-toxic inorganic or organic acid. Inorganic acids include, but are not limited to, hydrochloric, hydrobromic, hydroiodic, nitric, sulfuric, and phosphoric. Organic acids include, but are not limited to, aliphatic, aromatic, carboxylic, and sulfonic organic acids including, but not limited to, formic, acetic, propionic, succinic, benzoic camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, alginic, and galacturonic acid.

The term "half-life" is understood to mean the time in which the concentration of the SERM in the blood plasma is halved.

The term "intermittent administration" means a period of administration of a therapeutically effective dose of a SERM, followed by a time period of discontinuance, which is then followed by another period of administration of a therapeutically effective dose, and so forth. The administration period of the therapeutically effective dose may comprise continuous dosing, as for example with a sustained-release formulation, or may comprise daily, every other day, weekly, or there between, dosing, as for example, with one, two or more tablets per day, so long as the dosing interval during the administration period is less than the discontinuance period.

Long term oral administration of tamoxifen is associated with a ~3-fold increase in vascular-related thrombotic events including stroke, deep vein thrombosis and pulmonary embolisms. Long term administration of tamoxifen is also associated with a ~2-fold increase in the risk of developing endometrial cancer and also significantly increases the risk of developing cataracts. Similar adverse events have also been reported in connection with long term oral administration of raloxifen, albeit to a lesser extent.

The present inventors have surprisingly discovered that adverse side effects of long term oral SERM administration can be reduced or even eliminated without loss of efficacy in treating disorders which are responsive to SERMs. This reduction or elimination occurs when the SERM has a short half-life, thereby achieving therapeutic effect and, within a short time, falling to sub-therapeutic concentrations. By employing a SERM with a short half-life, it is possible to treat estrogen receptor-mediated conditions that benefit from chronic SERM administration with a reduced or eliminated possibility of serious adverse side effects. During long-term administration of SERMs with a long half life such as tamoxifen (5-7 days), the drug may extensively accumulate over time. Accordingly, in several embodiments, the present invention provides a method for long-term administration of a SERM, wherein the half-life of the SERM is about 30 hours or less, in order to treat an estrogen receptor-mediated condition thereby minimizing or even eliminating these adverse effects. Preferably the SERM has a half-life of less than 27 hours, such as less than 26, less than 25, less than 24, less than 23, less than 22, less than 21, less than 20, less than 19, less than 18, less than 17, less than 16, less than 15, less than 14, less than 13, less than 12, less than 11, and less than 10.5 hours.

Surprisingly, therapeutic benefit may be seen at the same (or possibly even lower) dosage and administration frequency observed for SERMs with a longer half life, such as tamoxifen, despite more rapid clearance from the body. The present inventors have discovered that a "correction" of the hypothalamic-pituitary-gonadal axis can occur following a brief initial "loading phase" of the SERM, thereby compensating for the decreased half-life and possibly allowing for even lower dosage and/or administration frequency to achieve equivalent therapeutic effect. In this respect, tamoxifen, representative of SERMs with relatively long half-lives, is prescribed in an oral formulation containing 10 mg to 20 mg of tamoxifen to be administered once or twice per day. Thus, in one aspect, the present invention provides a method for treating an estrogen receptor-mediated condition comprising long-term administration of a SERM with a half-life of 30 hours or less, preferably less than 27 hours, at a dosage of 20-40 mg or less per day, such as between 1 and 19 mg per day, between 5 and 19 mg per day, between 5 and 10 mg per day, or between 1 and 9 mg per day. In a related embodiment, the SERM with a half-life of 30 hours or less may be administered intermittently such as every other day, weekly, every other week, monthly, or at any dosing interval there between at a dosage of 20-40 mg or less, e.g. at a dosage between 1 and 19 mg, between 5 and 10 mg or between 1 and 9 mg. Intermittent administration of the SERM may be preceded by an initial loading phase in which the SERM is administered at 10-20 mg or less for a period of at least 7 (e.g. at least 14) or more consecutive days.

A SERM with a half-life of 30 hours or less, preferably with a half-life less than 27 hours, may be administered for a period of at least 6 months, at least one year, at least 18 months, at least 2 years, at least 30 months, at least 3 years, at least 42 months, at least 4 years, at least 54 months, or at least (e.g. more than) 5 years in order to treat an estrogen receptor-mediated condition.

Any known SERM with a half-life of 30 hours or less, preferably less than 27 hours, may be administered for a period of at least 6 months according to the present invention. A list of SERMs along with their half-lives is provided at Table 1:

TABLE 1

Half-life of Several Selective Estrogen Receptor Modulators

| SERM | Half-Life |
| --- | --- |
| Enclomiphene (trans-clomiphene) | 10.5 hours |
| Droloxifene | 24 hours |
| Levormeloxifene | 24 hours |
| (Deaminohydroxy)toremifene | 25-30 hours |
| Raloxifene | 27 hours |
| Bazedoxifene | 28 hours |
| Arzoxifene | 30 hours |
| Toremifene | 5 days |
| Tamoxifen | 5-7 days |
| Clomid | 5-7 days |
| Lasofoxifene | 6 days |
| Ormeloxifene | 7 days |
| Idoxifene | 3 weeks |

In a preferred embodiment, the SERM for use in the methods of the invention is selected from the group consisting of: droloxifene, trans-clomiphene, levormeloxifene, (Deaminohydroxy)toremifene, raloxifene, bazedoxifene and arzoxifene.

In another embodiment, a metabolite of trans-clomiphene with a relatively short half life is employed in the methods of the invention. The trans-clomiphene metabolite may be selected from 4-hydroxy-trans-clomiphene (4-OH-trans-clomiphene), 4'-hydroxy-trans-clomiphene (or 4'-OH-trans-clomiphene), 3-hydroxy-trans-clomiphene (or 3-OH-trans-clomiphene), 3,4-dihydroxy-trans-clomiphene, and N-desethyl-trans-clomiphene.

In another embodiment, the present invention relates to a method for identifying SERMs which have reduced or eliminated side effects when administered chronically by determining the half life of the SERM in the blood of a mammal, which is relevant for pharmacokinetic ratios in humans or in humans in phase I clinical trial development and comparing the half life of the SERM to that of tamoxifen. A SERM with reduced or eliminated side effects when administered chronically is identified if the SERM has a shorter half life than tamoxifen.

In various embodiments, the present invention also provides pharmaceutical compositions comprising one or more SERMs with a half-life of 30 hours or less or salts thereof as described and a pharmaceutically acceptable carrier, which can be used in the methods described herein.

In one embodiment, a method for elevating testosterone levels is provided comprising administering an effective amount of a SERM with a half-life of 30 hours or less or a salt thereof (or pharmaceutical composition comprising same) to a patient in need of such treatment for a period of at least 6 months. In a related embodiment, a method for treating a disorder related to testosterone deficiency including, without limitation, oligospermia, azoospermia, wasting and depression is provided. In a preferred embodiment the patient is a human male with secondary hypogonadism, in which case the SERM may be administered for a period of at least 6 months in order to treat the secondary hypogonadism.

In another embodiment, a method for decreasing cholesterol levels is provided, comprising administering an effective amount of a SERM with a half-life of 30 hours or less or a salt thereof (or pharmaceutical composition comprising same) to a patient in need of such treatment for a period of at least 6 months. In a preferred embodiment the patient is a human male with secondary hypogonadism In another embodiment, a method for treating and/or preventing a condition selected from the group consisting of benign prostate hypertrophy, prostate cancer and elevated triglycerides is provided comprising administering an effective amount of a SERM with a half-life of 30 hours or less or a salt thereof (or pharmaceutical composition comprising same) to a patient in need of such treatment for a period of at least 6 months. In a preferred embodiment the patient is a human male with secondary hypogonadism.

In another embodiment, a method for treating infertility in a human male is provided comprising administering an effective amount of a SERM with a half-life of 30 hours or less or a salt thereof (or pharmaceutical composition comprising same) to a human male in need of such treatment for a period of at least 6 months. In a preferred embodiment the patient is a human male with secondary hypogonadism.

In another embodiment, a method for preventing the transition from metabolic syndrome to type 2 diabetes is provided comprising administering an effective amount of a SERM with a half-life of 30 hours or less or a salt thereof (or pharmaceutical composition comprising same) to a human male with secondary hypogonadism for a period of at least 6 months.

In yet another embodiment, a method for treating type 2 diabetes mellitus is provided comprising administering an effective amount of a SERM with a half-life of 30 hours or less or a salt thereof (or pharmaceutical composition comprising same) to a human male in need of such treatment for a period of at least 6 months. Preferably, the human male is a human male with secondary hypogonadism.

In another embodiment, a method for the treatment of female infertility is provided comprising administering an effective amount of a SERM with a half-life of 30 hours or less or a salt thereof (or pharmaceutical composition comprising same) to a female in need of such treatment for at least six consecutive cycles. Preferably the SERM is administered as a daily dose in the early follicular phase of the menstrual cycle for five consecutive days. For example, an administration schedule could involve administration on days 5 to 9 or on days 3 to 7 of the menstrual cycle. Preferably the patient is an anovulatory female.

In another embodiment, a method for the treatment and/or prevention of breast cancer is provided comprising administering an effective amount of a SERM with a half-life of 30 hours or less or a salt thereof (or pharmaceutical composition comprising same) to a female in need of such treatment for a period of at least 6 months, preferably at least 5 years (e.g. more than 5 years). According to this embodiment, the SERM may be administered to a female at increased risk for developing breast cancer in order to prevent the development of breast cancer. Alternatively, the SERM may be administered to a female with breast cancer in order to treat the breast cancer. The SERM may also be administered as an adjuvant therapy following initial treatment with surgery in order to minimize the possibility of relapse. Preferably when administered as an adjuvant, the SERM is administered for a period of at least about 5 years.

In another embodiment, a method for the treatment of endometrial (or uterine) cancer is provided comprising administering an effective amount of a SERM with a half-life of 30 hours or less or a salt thereof (or pharmaceutical composition comprising same) to a female in need of such treatment for a period of at least 6 months.

In yet another embodiment, a method for the treatment of ovarian cancer is provided comprising administering an effective amount of a SERM with a half-life of 30 hours or less or a salt thereof (or pharmaceutical composition comprising same) to a female in need of such treatment for a period of at least 6 months.

In yet another embodiment, a method for treatment of osteoporosis is provided comprising administering an effective a SERM with a half-life of 30 hours or less or a salt thereof (or a pharmaceutical composition comprising same) to a female in need of such treatment for period of at least 6 months.

The SERMs used in the compositions and methods described herein can be chemically synthesized according to known methods and include the salt form of each of the compounds. Raloxifene, 6-hydroxy-2(4-hydroxyphenyl)-3-[4-(2-piperdinoethoxy)benzoyl]benzo[b]thiophene, and its pharmacologically acceptable salts may be produced according to the methods described in U.S. Pat. Nos. 4,418,068 and 4,133,814, each of which is incorporated herein by reference. Droloxifene, E-1-[4'-(2-dimethylaminoethoxy)phenyl]-1-(3'-hydroxyphenyl)-2-phenyl-1-butene, and its pharmacologically acceptable salts may be produced according to the methods described in U.S. Pat. No. 5,047,431, which is incorporated herein by reference. Arzoxifene, 2-(4-Methoxyphenyl)-4-[4-[2-(1-piperidinyl)ethoxy]phenyoxy]benzo[b]thiophene-6-ol, and its pharmaceutically acceptable salts may be produced according to the methods described in U.S. Pat. No. 5,723,474, which is incorporated herein by reference. Bazedoxifene and its pharmaceutically acceptable salts may be produced according to the methods described in U.S. Pat. Nos. 5,998,402 and 6,479,535, each of which is incorporated herein by reference. Levormeloxifene, (−)-3R,4R-trans-7-methoxy-2,2-dimethyl-3-phenyl-4-{4-[2-(pyrrolidin-1-yl)ethoxy]phenyl}chromane, and its pharmaceutically acceptable salts may be produced according to the methods described in U.S. Pat. No. 4,447,622, which is incorporated herein by reference.

Pharmaceutical compositions according to the present invention may comprise or consist essentially of a SERM of the invention at a dosage between about one mg to about 200 mg (although the determination of optimal dosages is with the level of ordinary skill in the art). The composition may comprise a SERM of the invention at a dosage of about 1 mg, 2 mg, 3, mg, 4 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg, 200 mg or there between. In a preferred embodiment, the composition comprises a SERM of the invention at a dosage of about 1 mg to about 19 mg, more preferably at a dosage of about 1 mg to about 9 mg.

Pharmaceutical compositions may comprise 100% w/w of a SERM of the invention or may additionally comprise other active agents useful in achieving the desired therapeutic effect. Where the pharmaceutical composition comprises 100% w/w of a SERM of the invention, one or more additional active agents may be separately co-administered sequentially or simultaneously to achieve a desired therapeutic effect. Thus, in several embodiments, the present invention provides a method for treating an estrogen receptor-mediated condition comprising co-administering a SERM of the invention with an additional therapeutic agent. The additional therapeutic agent may be any agent known to be effective in treating the estrogen receptor-mediated condition.

The terms "treat" or "treatment" as used in the instant application, refer to both therapeutic treatment and prophylactic or preventative measures, wherein the object is to prevent or slow down (lessen) an undesired physiological or psychological change or disorder, such as symptoms associated with secondary hypogonadism. For purposes of the present invention, beneficial or desired clinical results include, but are not limited to, alleviation of symptoms, diminishment of extent of disease, stabilized (i.e., not worsening) state of disease, delay or slowing of disease progression, amelioration or palliation of the disease state and remission (whether partial or total), whether detectable or undetectable. "Treatment" can also mean prolonging survival as compared to expected survival if not receiving treatment. Individuals in need of treatment include those already with the condition or disorder as well as those prone to develop the condition or disorder or those in whom the condition or disorder is to be prevented.

Suitable pharmaceutical compositions or unit dosage forms may be in the form of solids, such as tablets or filled capsules or liquids such as solutions, suspensions, emulsions, elixirs or capsules filled with the same, all for oral use. The compositions may also be in the form of sterile injectable solutions or emulsions for parenteral (including subcutaneous) use. The compositions may also be foiinulated for topical administration. For example, the composition may be formulated as a lotion, cream, ointment, gel, foam, or transdermal patch. In one preferred embodiment, the composition is formulated as a gel (e.g. an aqueous alcoholic gel) for transdermal administration (e.g. to the scrotum). Such pharmaceutical compositions and unit dosage forms thereof may comprise ingredients in conventional proportions.

Although oral administration is the preferred route, compositions according to the present invention may be administered by any route of administration including, but not limited to, intravenous, subcutaneous, buccal, transmucosal, intrathecal, intradermal, intracisternal, intramuscular, transdermal, intraperitoneal, epidural, vaginal, rectal, intranasal, sublingual, intra-articular, intra-cerebrospinal and intrasynovial.

Compositions of the present invention may also be administered in fast-release formulations, slow-release formulations or mixtures of fast-release and slow-release formulations such as a multi-layer tablet comprising at least one fast-release layer and at least one slow-release layer.

All of the references discussed herein are incorporated by reference in their entirety.

The following Examples are meant to be illustrative of the invention and are not intended to limit the scope of the invention as set out is the appended claims.

EXAMPLE 1

Pharmacokinetic Profile of Trans-Clomiphene

A clinical study to estimate the pharmacokinetic (PK) profile of enclomiphene (trans-clomiphene) following single-dose and steady-state doses administered orally. 52 adult males between 18 and 75 years of age with total serum testosterone level <250 ng/dl or between 250 to 300 ng/dl and FSH/LH levels within the nomial range, were randomly assigned to one of the following five treatment groups: (i) 12.5 mg enclomiphene/day (ii) 25 mg enclomiphene/day (iii) 50 mg enclomiphene/day (trans-clomiphene) (iv) Androgel® (1% topical testosterone applied daily) or (v) placebo. Enclomiphene citrate was provided as 12.5 mg capsules and orally administered once (12.5 mg arm) twice (25 mg arm) or four times (50 mg arm) per day for 14 consecutive days. Single-dose and steady-state PK assessments were preformed in a subset of these males following the first (Day 1) and last (Day 14) dose. On Days 1 and 14, serial blood samples were obtained pre-dose (0 hours) and at 0.5, 1, 2, 3, 4, 6, 8, 12, 18 and 24 hours post-dose for plasma enclomiphene determination. Pre-dose plasma enclomiphene concentrations were also measured on Day 11 using a single blood sample. Pharmacokinetic (PK) endpoints were area under concentration time curve from zero to 24 hours ($AUC_{0-24}$), maximum concentration ($C_{max}$), time to $C_{max}$ ($T_{max}$) and the elimination half-life ($t_{1/2}$) of plasma enclomiphene following single dose administration on Day 1 and steady-state dosing on Day 14. PK parameters were calculated using noncompartmental methods for subjects randomized to enclomiphene. The accumulation ratio, defined as the $AUC_{0-24}$ on Day 14, divided by the $AUC_{0-24}$ value on Day 1 was calculated.

On Day 1, mean (SD) $C_{max}$ values for enclomiphene 12.5 mg, 25 mg and 50 mg were 1.98 (1.78), 4.79 (3.88) and 5.56 (1.09) ng/ml respectively. On Day 14, mean (SD) $C_{max}$ values for enclomiphene 12.5 mg, 25 mg and 50 mg were 2.68 (1.68), 10.63 (9.58) and 12.09 (5.74) ng/ml respectively.

. On Day 1, median $T_{max}$ values for enclomiphene 12.5 mg, 25 mg and 50 mg were 4.0, 2.0 and 2.0 hours, respectively, On Day 14, median $T_{max}$ values for enclomiphene 12.5 mg, 25 mg and 50 mg were 4.0, 3.0 and 2.0 hours respectively.

On Day 1, mean (SD) $T_{1/2}$ values for enclomiphene 12.5 mg, 25 mg, and 50 mg were 7.91 (4.91), 8.08 (2.01) and 6.53 (0.92) hours, respectively. On Day 14, mean (SD) $T_{1/2}$ values for enclomiphene 12.5 mg, 25 mg and 50 mg were 9.31 (2.40), 10.73 (2.51) and 9.69 (0.92) hours, respectively.

The accumulation index for each enclomiphene dose group was calculated based on the arithmetic mean of the individual ratio of $AUC_{(0-24)}$ on Day 14 divided by $AUC_{(0-24)}$ on Day 1. Mean (SD) accumulation index values for enclomiphene 12.5 mg, 25 mg and 50 mg were 2.53 (1.08), 2.84 (1.19) and 2.49 (0.63), respectively.

The PK results are depicted in FIG. 1. Based on the PK data obtained, the half life of enclomiphene was determined to be ~10.5 hours.

EXAMPLE 2

Long Term Administration of Tans-Clomiphene 104 adult human males with secondary hypogonadism (serum testosterone <300 ng/dl at the initial screening visit) who completed a six month study in which trans-clomiphene (citrate) was administered orally at dose of 12.5, 25 or 50 mg trans-clomiphene per day, were enrolled in a one year open label, multi-center extension study, with a total of 70 subjects completing the study. The overall mean age of subjects was 54.1 years of age with a body mass index (BMI) of 31.8 kg/m² and mean baseline total testosterone of 290.1 ng/dL. Subjects in the six month study had been randomly assigned to the following groups: (1) 12.5 mg trans-clomiphene (2) 25 mg trans-clomiphene (3) 50 mg trans-clomiphene (4) Andro- Gel® 1% topical testosterone or (5) placebo. All subjects in the extension study received a daily oral dose of 12.5 mg trans-clomiphene for up to one year. Adverse events as well as change from baseline in a variety of clinical parameters were assessed in patients rolling over from each of the five treatment groups in the six month study during the course of the extension study. Assessments were made during laboratory visits which occurred at Day 0 [Visit 1], Month 1 [Visit 2] and at approximately 2-month intervals thereafter for 12 months (Month 1 [Visit 2] to Month 12 [Visit 7]). A follow up visit [Visit 8] occurred one month after cessation of treatment.

The primary efficacy endpoint of the study was the proportion of subjects at 1 year who showed morning total serum testosterone concentrations within the normal range (300-1040 ng/dl). A single morning's testosterone level has been shown to correlate highly to both maximum and average testosterone levels observed for a given subject. Overall, 62.5% of subjects had mean total serum testosterone levels within the normal reference range at 1 year. Overall mean increases in total serum testosterone from baseline to 1 year were statistically significant; during the study, overall mean increases in total testosterone concentration from baseline ranged from 9.8 to 251.3 ng/dl (Months 2 to follow-up visit inclusive).

Statistically significant improvements in libido were observed from baseline at months 4, 6 and 12 as assessed on the libido component of the International Index of Erectile Function (IIEF) questionnaire. However, no concomitantly significant changes were reflected in other questionnaires of sexual function such as the DeRogatis Interview for Sexual Function (DISF-SR II (M)) and Male Sexual Distress Scale IV-A (MSDS). During the study overall increases in testicular size mean values (measured using an orchidometer) ranged from 0.8 to 2.3 mL; a statistically significant increase was observed at Month 6 only.

Statistically significant increases in LH, FSH, sex hormone binding globulin (SHBG), estradiol, dihydrotestosterone (DHT) and DHT/testosterone ratio were observed at the majority or all of the timepoints; statistically significant decreases in prolactin were observed at the majority or all of the timepoints.

Statistically significant decreases in total cholesterol (TC), high-density lipoprotein cholesterol (HDL-C) and triglycerides from baseline were observed at the majority or all of the timepoints.

Only five (5) subjects experienced serious adverse effects (SAEs)—four of the five subjects had SAEs considered unrelated/unlikely related to the drug. Overall, 51.5% of subjects experienced at least one adverse event during the study; 18.8% of subjects (19/101) experienced at least one adverse event that was considered related to the study drug. The majority of events were mild or moderate in severity; nine subjects experienced events that were considered severe. Nine subjects discontinued from the study due to AEs. Five of the 9 subjects who discontinued from the study experienced AEs that were considered possibly or probably related to study drug.

No subjects were discontinued due to a reduction in visual acuity.

Although clinically significant changes in some blood chemistry variables were observed in a small number of subjects, only one subject was discontinued from the study due to AEs of alanine aminotransferase (ALT) and aspartate aminotransferase (AST) increased. There were no clinically relevant changes in hematology, blood chemistry or urinalysis variables, or in vital signs, physical exam, prostate-specific antigen (PSA) values or electrocardiogram (ECG) readings.

These findings strongly support the efficacy of long term oral administration of SERMs with relatively long half lives at low concentrations for treating a variety of estrogen receptor mediated conditions while reducing or eliminating the serious adverse effects observed when SERMs with relatively long half lives (e.g. tamoxifen) are chronically administered. Over the course of 18 months of treatment with 12.5 mg oral trans-clomiphene, the cardiovascular and ocular adverse effects observed during long term administration of tamoxifen (e.g. deep vein thrombosis, cataracts) were not observed. This data is consistent with animal safety pharmacology studies in rodent, baboon, rabbit and dog models which demonstrated no adverse effects in the central nervous, respiratory or cardiovascular systems in animals administered trans-clomiphene.

The invention claimed is:

1. A method for treating an estrogen receptor-mediated condition selected from secondary hypogonadism, type 2 diabetes and infertility consisting essentially of orally administering a selective estrogen receptor modulator (SERM) or a pharmaceutically acceptable salt thereof selected from the group consisting of droloxifene, levormeloxifene, (Deaminohydroxy)toremifene, raloxifene, bazedoxifene and arzoxifene for a period of at least 6 months at a dosage of between 1 and 19 mg per day or every other day to a patient in need of such treatment.

2. The method of claim 1, wherein the SERM is administered at a dosage of between 1 and 10 mg per day.

3. The method of claim 1, wherein the SERM has a half-life of less than 27 hours.

4. The method of claim 3, wherein the SERM is selected from the group consisting of droloxifene, levormeloxifene, and (Deaminohydroxy)toremifene.

5. The method according to claim 1, wherein the SERM is administered daily.

6. The method of claim 1, wherein the SERM is administered to the patient for a period of more than 5 years.

7. The method of claim 1, wherein the patient is a human male with a serum testosterone level below 300 ng/DL.

8. The method of claim 1, wherein the SERM is administered to an anovulatory female for at least 4 consecutive cycles, each cycle comprising an administration period of five consecutive days beginning on the second to fifth day after the onset of spontaneous or induced menstruation.

9. The method of claim 8 wherein the female is anovulatory.

10. The method according to claim 1, wherein the SERM is administered to treat type 2 diabetes in a human male.

11. The method according to claim 1, wherein the salt of the SERM is a citrate salt.

12. The method of claim 1 wherein the SERM is administered at a dosage of 1 to 9 mg per day.

* * * * *